United States Patent [19]

Soderstrom et al.

[11] Patent Number: 4,563,348

[45] Date of Patent: Jan. 7, 1986

[54] SEC-BUTYL (Z)-7-TETRADECENOATE AND ITS USE AS A SEX ATTRACTANT FOR THE GRAPELEAF SKELETONIZER

[75] Inventors: Edwin L. Soderstrom, Fresno; William F. Haddon, Larkspur; Joel Myerson, Belmont, all of Calif.

[73] Assignee: The United States of America as represented by the Secretary of Agriculture, Washington, D.C.

[21] Appl. No.: 462,491

[22] Filed: Jan. 31, 1983

[51] Int. Cl.$^4$ ............... A01N 25/00; C11B 11/00; C11B 1/00

[52] U.S. Cl. .................. 424/84; 260/405.5; 260/410.9 R; 514/549

[58] Field of Search ............... 424/312, 84; 260/405.5, 260/410.9 R, 410.9 D; 514/549

[56] References Cited

PUBLICATIONS

Francke et al., Isopropyl Esters of Carboxylic Acids–A New Class of Insect Pheromones, Chem. Abstracts, vol. 91, No. 207727s, 1979.

Batchelor et al., Occurence of Cis-7-Tetradecenoic Acid in the Envelop Phospholipids of *Escherichia coli* K12, Chem. Abs., vol. 79, No. 89212x, 1973.

Kimble et al., Comparison of the Fatty Acids of Proteolytic Type B and Non–Proteolytic Types E and F of *Clostridium botulinum*, Chem. Abstracts, vol. 72, No. 10025n, 1970.

M. M. Barnes, D. W. Robinson and A. G. Forkes, "Attractants for Moths of the Western Grape Leaf Skeletonizer," *Journal of Economic Entomology*, vol. 47, pp. 58–63, (1954).

David G. Sullivan, "Characterization of the Western Grapeleaf Skeletonizer," (*Harrisina brillians*, B & McD.; Family Zygaenidae) Pheromone(s), 1975, (unpublished).

*Primary Examiner*—Thomas A. Waltz
*Attorney, Agent, or Firm*—M. Howard Silverstein; David G. McConnell; Margaret A. Connor

[57] ABSTRACT

A pheromonal compound produced by the western grapeleaf skeletonizer has been identified as sec-butyl (Z)-7-tetradecenoate. The synthetically-prepared compound demonstrates activity toward both the western grapeleaf skeletonizer, *Harrisina brillians* Barnes and McDunnough and the grapeleaf skeletonizer, *Harrisina americana* (Guerin). By attracting adult moths to field traps, this compound offers a useful tool in monitoring and control of this pest.

13 Claims, No Drawings

SEC-BUTYL (Z)-7-TETRADECENOATE AND ITS USE AS A SEX ATTRACTANT FOR THE GRAPELEAF SKELETONIZER

BACKGROUND OF THE INVENTION

1. Field of the Invention

This invention relates to a novel compound useful as a sex attractant for the grapeleaf skeletonizer, Harrisina species (Lepidoptera: Zygaenidae). The invention relates further to use of this compound in combination with or integration with other insect control agents such as insecticides, parasites, predators and pathogens to simultaneously attract and combat the skeletonizer.

2. Description of the Prior Art

Insects of the group known as the grapeleaf skeletonizer, Harrisina species (Lepidoptera: Zygaenidae) are pests of vineyards, backyard grapevines, wild grapes as well as some ornamental plants such as Virginia creeper and Boston ivy and occasionally, fruit trees. In addition to defoliating grapevines and feeding on the fruit, the skeletonizer has urticating setae which can produce skin welts on vineyard workers.

In California, the western grapeleaf skeletonizer (WGLS), *Harrisina brillians* Barnes and McDunnough, poses a threat to commercial grape production. For years chemical pesticide sprays used to control other insects have controlled the skeletonizer in commercial vineyards, but the intensive use of conventional chemicals may ultimately present hazards to man and the environment. Furthermore, intensive use of insecticides to control other insect pests has frequently resulted in the survival of insecticide-resistant insect populations that can no longer be treated effectively, thus methods of pest control which offer an alternative to the conventional use of insecticides are needed. Although at present in California infestations of the skeletonizer are in backyard plantings or wild grapes that are not treated adequately with insecticides, a major escalation of the economic effect of this insect could occur if it becomes resistant to insecticides and invades commercial vineyards.

The continued search for alternatives to the widespread application of insecticides has led to the investigation of sex attractants as potential agents for use in integrated pest management. A number of economically important insects are currently monitored and at least partially controlled by use of their own specific sex pheromone. In the case of the grapeleaf skeletonizer, although Barnes et al., *Journal of Economic Entomology*, Volume 47, pp 58–63 (1954), reported that male western grapeleaf skeletonizer moths were attracted to extracts of WGLS females, the lack of identification and commercial availability of a skeletonizer pheromone has precluded application of this technology to the treatment of this pest.

SUMMARY OF THE INVENTION

We have now for the the first time obtained in pure or substantially pure form the major female-produced sex pheromone of the western grapeleaf skeletonizer. This new compound, identified as sec-butyl (Z)-7-tetradecenoate (sec-B (Z)-7-T) has been isolated from females of the western grapeleaf skeletonizer (WGLS), *Harrisina brillians* Barnes and McDunnough and has also been successfully synthesized. It is an effective attractant for WGLS males as well as males of the grapeleaf skeletonizer (GLS), *Harrisina americana* (Guerin).

Our invention provides means for detection of the skeletonizer and provides potential for population control and population density estimation of this pest. Its usefulness in eliciting a behavioral response when applied to a locus of skeletonizer males suggests the following economic applications of the attractant: (1) the detecting of infestation outbreaks; (2) the monitoring of existing adult populations in order to predict infestation levels the following year for scheduling of treatment with larval insecticides and (3) the control of reproduction in adult populations either by direct disruption of mating through confusing or inhibitory properties, or by attracting a demographically significant portion of the male population for subsequent destruction or sterilization.

In accordance with this discovery, it is an object of the invention to identify for the first time a sex pheromone from a representative of the genus Harrisina, and more particularly from the species *brillians*.

A further object of the invention is to produce sec-butyl (Z)-7-tetradecenoate as a synthetic counterpart of the natural WLGS sex pheromone and as a sex attractant for use in attracting other species of the grapeleaf skeletonizer.

Another object of the invention is to utilize sec-butyl (Z)-7-tetradecanoate as a detection, monitoring or control agent for the grapeleaf skeletonizer.

A further object is to provide a grapeleaf skeletonizer attractant for use with insecticides, biological control agents and the like to attract and combat the skeletonizer.

Other objects and advantages of the invention will be evident from the following description where in parts and percentages are by weight.

DETAILED DESCRIPTION OF THE INVENTION

Sec-butyl (Z)-7-tetradecenoate was identified by chemical, spectroscopic and chromatographic techniques as the major component of volatiles emitted by WGLS female moths. This compound produced wing flutter, hair pencil display and dancing in male WGLS moths in laboratory tests and was highly attractive to WGLS males in field tests as shown in Examples 3–5 below. It has also been shown to be an attractant for grapeleaf skeletonizer (GLS), *Harrisina americana* (Guerin) males. Its ability to attract GLS males as well as WGLS males suggest that its biosynthesis is not limited to the WGLS species and that it may be a sex attractant of the United States Harrisina species, *Harrisina coracina* (Clemens) as well as grapeleaf skeletonizers found outside the United States.

Three other compounds were identified in the volatiles emitted by WGLS female moths—isopropyl (Z)-7-tetradecenoate, sec-butyl decanoate and sec-butyl dodecanoate. Secondary butyl or isopropyl unsaturated esters have never before been reported from the volatile complex of a lepidopteran species, thus our identification has resulted in the discovery of a new structural class of insect volatiles. Both sec-B (Z)-7-T and isopropyl (Z)-7-tetradecenoate are novel compounds.

Field tests of sec-B (Z)-7-T versus an equal amount of sec-B (Z)-7-T contained in a mixture of the other three insect volatiles in the ratio found in the natural extract showed that sec-B (Z)-7-T alone has the same attractancy as the mixture, suggesting that it is the only pheromone component.

The sec butyl (Z)-7-tetradecenoate compound of this invention is characterized by the following structural formula:

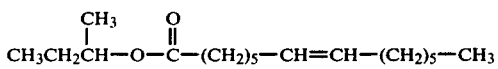

It is apparent therefrom that the compound may exist as either of two stereoconfigurations by virtue of the chiral center denoted by the *. The amount of R- or S-enantiomer in the natural isolate is not known, however tests of the synthetically produced R,S-compound show that it is very highly attractive to WGLS males (100 μg of a crude synthetic preparation had the attractancy of about four female moths as described in detail in Example 4 below). This is important as the inherent difficulty and expense of producing a pure enantiometer by directed stereochemical synthesis favors the synthetic racemic sec-B (Z)-7-T for commercial utilization. Field tests also indicate that sec-B (Z)-7-T is very specific to the skeletonizer; no insects other than the skeletonizer were attracted in amounts greater than those in the control.

As previously discussed, the synthetic pheromone may be used as a detecting agent, monitoring agent or control agent for grapeleaf skeletonizers. In practice, sec-B (Z)-7-T is used as a trap bait or is otherwise applied to a locus of the adults in an amount effective to induce the desired response. In the case of an attractant response, for example, an effective amount is defined as that quantity of agent which attracts skeletonizer males to the location of a bait at a rate significantly higher than males are attracted to a nonbaited location. Factors such as population density, temperature, wind velocity and release rate will influence the actual numbers of skeletonizers trapped.

It is envisioned that sec-B (Z)-7-T would be effective in detecting, monitoring or controlling skeletonizer populations when used in conjunction with any type of trap or pheromone disseminator known in the art. Typically, the compound would be applied to the device in solution with hexane or other suitable carrier. Volatilization can be retarded by inclusion of a diluant and/or extender such as trioctanoin. Slow release may also be effected by encapsulation or absorption into a porous substrate.

When used as a detection or monitoring agent, traps are baited with the attractant of the invention and the catch tabulated to determine size and location of infestation. Economic use of appropriate pest management systems can then be determined.

Use of the attractant of the invention as a control agent can be carried out in several ways. One method is to use the compound to attract the insects to suitable substrates and subsequently or simultaneously expose the insects to insecticides which control the skeletonizer. A second method is to detect the location and boundaries of localized skeletonizer infestations and employ in the area biological control agents, e.g., parasites such as the wasp, *Apanteles harrisinae* Muesbeck or fly, *Ametadoria* (=*Sturmia*) *harrisinae* (Coquillet); predators or pathogens. This method eliminates the need to spread the control agents unnessarily and helps prevent killing useful insects and other animals.

The attractant may also be used to control the skeletonizer by confusion of males, thus preventing mating. For example, one technique is to permeate the atmosphere with the pheromone to prevent the males of the species from orienting to and inseminating the females.

Other uses of the attractant will be obvious to those in the art.

EXAMPLES

The following examples are intended only to further illustrate the invention and are not intended to limit the scope of the invention which is defined by the claims.

EXAMPLE 1

Isolation and Identification of Volatiles From Female Western Grapeleaf Skeletonizers The volatiles from female western grapeleaf skeletonizers were collected by two methods. In the first method, 117 female moths were confined in a 1.5 liter collection chamber and the volatiles collected during a period of six days as follows: a vacuum source was applied to the end of a 6 inch by ¼ inch stainless steel tube filled with Tenax (a polyphenolether polymer gas chromatography absorbent made by Applied Science Laboratory); air entering the chamber (about 100 cc/min) passed an activated charcoal filter, passed through the chamber and entered the Tenax trap. The trap was eluted with 5 ml of ether, the ether evaporated and the residue dissolved in hexane and subjected to gas chromatography/mass spectroscopy analysis using a 42 m×0.25 mm I.D. pyrex OV-101 (methyl silicone stationary phase) column.

The presence of the following four compounds was conclusively identified and the proportion of each was determined to be: sec-butyl decanoate (15), sec-butyl dodecanoate (7), sec-butyl (Z)-7-tetradecenoate (56) and isopropyl (Z)-7-tetradecenoate (22). The major component, sec-butyl (Z)-7-tetradecenoate, exhibited sex pheromone activity as shown in Example 3 below. No sec-butyl (E)-7-tetradecenoate was detected in the volatiles.

The synthesized racemic mixture and the pheromone isolated from WGLS females gave identical mass spectra (electron ionization, 70 electron volts). The abbreviated spectrum (mass and abundance of most intense peak per 14 mass unit interval) is: 29 (30), 43 (44), 55 (100), 69 (75), 83 (56), 95 (40), 109 (30), 123 (16), 137 (9.6), 151 (8.1), 166 (10), 179 (3.2), 191 (7.1), 209 (42), 226 (9.0), 282 (3.6). An accurate mass of 282.2578, measured for the insect-produced pheromone, indicated a molecular formula of $C_{18}H_{34}O_2$ (calc. 282.2558). The synthetic and isolated pheromone gave identical Kovat's retention index values.

An additional amount of insect extract was obtained by dipping the abdomens of 40 adult females in 0.5 ml of hexane. The resulting mixture was filtered to remove insect scales, concentrated and analyzed by GC/MS as described above. The four esters described above were identified in the extract.

EXAMPLE 2

Synthesis of Sec-butyl (Z)-7-tetradecenoate

Tetrahydropyranyl ether derivative of hexamethylenebromohydrin. To a cooled solution of hexamethylenebromohydrin (30.0 g) and p-toluenesulfonic acid (1.89 g) in ether (130 ml) was added slowly 20.9 g of dihyropyran. The mixture was allowed to warm to room temperature after 1 hour. The reaction mixture was poured into saturated Na$_2$CO$_3$ solution, washed with water and brine, and the ether layer was dried with anhydrous Na$_2$SO$_4$. Removal of solvent under reduced pressure gave 44.7 g of a yellow liquid. Distillation (101°/0.1 torr) gave 15.5 g of the tetrahydropyranyl ether derivative of hexamethylenebromohydrin.

Tetrahydropyranyl ether derivative of 7-tetradecyne-1-ol. To a cooled solution (−15° C.) of 1-octyne (7.95 g) in 30 ml of dry tetrahydrofuran under a nitrogen atmosphere was added dropwise 30.4 ml of 2.09M butyllithium in hexane. The addition took 30 minutes, after which the reaction was warmed to 0° C. and then cooled to −10° C. This solution was added slowly to a cold (0° C.) solution of the tetrahydropyranyl ether derivative of hexamethylene bromohydrin (14.80 g) in 50 ml of hexamethylphosphoric triamide under nitrogen. The reaction mixture was allowed to warm to room temperature, stirred overnight, poured into cold water, and extracted three times with hexane. The combined organic layers were washed with water (three times) and brine, and dried with anhydrous Na$_2$SO$_4$. Removal of solvent under reduced pressure yielded 18.55 g of impure tetrahydropyranyl ether derivative of 7-tetradecyne-1-ol as a yellow oil. This material was used without further purification in the next step.

7-Tetradecyne-1-ol. The crude tetrahydropyranyl ether derivative of 7-tetradecyne-1-ol (18.39 g) and pyridinium p-toluene sulfonate (1.26 g) were dissolved in 500 ml of methanol and refluxed for 1.5 hours. The methanol was concentrated under reduced pressure, diluted with pentane, and washed with a 1:1 mixture of water and saturated. NaCl solution. The organic phase was concentrated and cooled in a dry ice/acetone bath. The resulting yellow solid was quickly filtered, giving 8.63 g of 7-tetradecyne-1-ol as a solid that melted below room temperature.

7-Tetradecynoic acid. A solution of 7-tetradecyne-1-ol (2.10 g) in acetone (100 ml) was added dropwise to a vigorously stirred solution of 20 ml of 1M CrO$_3$ in 10N H$_2$SO$_4$ cooled in ice. The addition took 30 hours after which 5 ml of isopropyl alcohol was added and the reaction mixture was filtered. The filtrate was diluted with 50 ml of water and extracted five times with ether. The combined organic phases were washed with water and saturated NaCl solution. The ether solution was then washed two times with 2N NaOH. The combined basic washes were extracted again with ether and acidified with 6 N HCl. Extraction with CHCl$_3$ (3 times), drying (MgSO$_4$) and removal of solvent under reduced pressure gave 1.95 g of 7-tetradecynoic acid as a yellow oil, which solidified on standing.

Sec-Butyl 7-tetradecynoate. A solution of 7-tetradecynoic acid (1.22 g) and BF$_3$-etherate (1 ml) in 20 ml of sec-butyl alcohol was refluxed for 18 hours. The solution was diluted with ether and washed with saturated Na$_2$CO$_3$ solution, water, 2N NaOH, water, and saturated NH$_4$Cl solution. The ether layer was dried (MgSO$_4$) and the solvent removed under reduced pressure to give 1.30 g of sec-butyl 7-tetradecynoate as a yellow liquid.

Sec-Butyl (Z)-7-tetradecenoate. Preparation of P-2 nickel hydrogenation catalyst: 4.46 ml of a 0.1N ethanolic solution of nickelous acetate was added to 40 ml of ethanol. To this rapidly stirred solution under a nitrogen atmosphere was added 4.46 ml of 0.1N ethanolic NaBH$_4$. Eleven ml of a 0.1N ethanolic ethylene diamine solution was added as a catalyst modifier.

The ester sec-butyl 7-tetradecynate (1.25 g) was added to the catalyst mixture and the system was charged with hydrogen. After 24 hours, the reaction mixture was filtered through celite and activated charcoal, diluted with ether, and washed with water and brine. The ether layer was dried (MgSO$_4$) and removal of solvent under reduced pressure gave 1.07 g of crude sec-butyl (Z)-7-tetradecenoate. This material was of sufficient purity (less than 3 percent E-isomer) to use directly for insect trapping, or it could be further purified by gas-liquid chromatography. The mass spectrum of this compound was identical to the spectrum of the major peak of the natural material.

EXAMPLE 3

Sex Attractancy of Sec-butyl (Z)-7-tetradecenoate

The sex attractancy of the western grapeleaf skeletonizer, *Harrisina brillians* Barnes and McDunnough to synthetic sec butyl (Z)-7-tetradecenoate and a synthetic mixture of the components identified in the natural extract in the proportion described in Example 1 was tested as follows: 100 μg of sec-B (Z)-7-T in hexane and a quantity of the mixture in hexane containing 100 μg of sec-B (Z)-7-T were each placed on a 1 cm$^2$ piece of double thick vinyl-coated fiberglass window screen and the screen hung in the center of a wing trap (sold under the tradename Pherocon ® 1C by Zoecon). The traps were located under a grape arbor five meters apart and were position rotated on a daily basis. Trapping was for eight days and was replicated three times. Blank traps with or without hexane were omitted as prior tests showed no moth attractancy.

The number of male moths attracted by sec-butyl (Z)-7-tetradecenoate was 31/trap/day; the mixture attracted 28/trap/day indicating that sec-B (Z)-7-T is as effective alone as the mixture and suggesting that the only compound which is a pheromone is sec-butyl (Z)-7-tetradecenoate.

EXAMPLE 4

Comparison of the Sex Attractancy of Synthetic Sec-butyl (Z)-7-tetradecenoate with WGLS Female Moths A test was set up to compare the attractancy of two female moths with 100 μg of sec butyl (Z)-7-tetradecenoate. Female moths of the western grapeleaf skeletonizer, *H. brillians.*, were field collected and were 24–48 hours emerged when placed for testing. Two females were placed in a 5 × 8 cm tetrahedral cage constructed of vinyl-coated fiberglass window screen closed by heat sealing and placed in a trap as described in Example 3. Synthetic sec-B (Z)-7-T (100 μg) was placed per 1 cm$^2$ screen as described in Example 3. Three traps containing female moths and three traps containing sec-B (Z)-7-T were placed in a vineyard naturally infested with WGLS, about 20 meters apart and within the vines, about 1.2 meters above ground level. The traps were randomly placed and rearranged daily. They were monitored from 6:30 a.m. through 10:30 a.m. Each test was replicated three times.

The relative attraction and capture of WGLS male moths to the females (194/trap/capture period (day)) was 36 percent versus 64 percent to synthetic sec-B (Z)-7-T (312/trap/capture period (day)) indicating that 100 μg of sec-B (Z)-7-T equals approximately four females in attractancy.

EXAMPLE 5

Dosage Tests of Sec-butyl (Z)-7-tetradecenoate

Traps described in Example 3 containing 0, 100, 1,000 or 10,000 μg of sec-B (Z)-7-tetradecenoate in hexane were placed in a vineyard about 20 meters apart and within the vines, about 1.2 meters above ground level. The traps were randomly placed and rearranged daily. A test consisted of 1 trap at each of the four concentrations on four consecutive trapping days in which each of the traps was placed in all four positions. The tests were replicated three times.

Results of the test indicated that the attractancy of sec-B (Z)-7-T increases with increasing amounts of compound. The data is tabulated below:

|  | Concentration (μg) | | | |
| --- | --- | --- | --- | --- |
|  | 0 | 100 | 1,000 | 10,000 |
| Average number captured per trap per day | 0.1 | 11.7 | 36.2 | 51.9 |

Having thus described the invention, we claim:

1. The substantially pure compound sec-butyl (Z)-7-tetradecenoate.

2. The compound of claim 1 which has been synthetically prepared.

3. The compound of claim 1 as the racemic mixture of its R- and S-enantiomers.

4. A sex attractant composition for the grapeleaf skeletonizer, Harrisina species, which comprises an effective attractant amount of the substantially pure compound sec-butyl (Z)-7-tetradecenoate and a carrier.

5. The attractant composition of claim 4 in combination with an effective amount of a control agent for the grapeleaf skeletonizer, Harrisina species.

6. The attractant composition of claim 5 wherein said control agent is an insecticide for the grapeleaf skeletonizer, Harrisina species.

7. The attractant composition of claim 5 wherein said control agent is a predator, parasite or pathogen of the grapeleaf skeletonizer, Harrisina species.

8. A method of eliciting a behavioral response in a grapeleaf skeletonizer, Harrisina species adult comprising applying to the locus thereof an effective amount of sec-butyl (Z)-7-tetradecenoate.

9. The method of claim 8 wherein said Harrisina species is a species from the group consisting of *H. brillians* and *H. americana*.

10. The method of claim 8 where said tetradecenoate is synthetically prepared.

11. The method of claim 8 wherein said tetradecenoate is in combination with a suitable carrier therefore.

12. The method of claim 8 wherein said tetradecenoate is in combination with an effective amount of a control agent for the grapeleaf skeletonizer, Harrisina species.

13. The method of claim 12 wherein said control agent is an insecticide for the grapeleaf skeletonizer, Harrisina species.

* * * * *